United States Patent
Dworak et al.

(10) Patent No.: US 7,086,267 B2
(45) Date of Patent: Aug. 8, 2006

(54) METAL-FORMING DIE AND METHOD FOR MANUFACTURING SAME

(75) Inventors: Bruce E. Dworak, Cromwell, CT (US); Frank W. Dworak, 329 Pleasant Valley Rd., Rocky Hill, CT (US) 06067

(73) Assignee: Frank W. Dworak, Rocky Hill, CT (US)

( * ) Notice: Subject to any disclaimer, the term of this patent is extended or adjusted under 35 U.S.C. 154(b) by 0 days.

(21) Appl. No.: 10/899,819

(22) Filed: Jul. 27, 2004

(65) Prior Publication Data

US 2005/0178182 A1 Aug. 18, 2005

Related U.S. Application Data

(63) Continuation-in-part of application No. 10/782,151, filed on Feb. 18, 2004, now Pat. No. 6,953,138.

(51) Int. Cl.
*B21D 37/00* (2006.01)
*B21D 37/20* (2006.01)

(52) U.S. Cl. .............. 72/413; 72/478; 72/412; 76/107.1

(58) Field of Classification Search .......... 72/416, 72/413, 412, 469, 478; 76/13, 14, 107.1
See application file for complete search history.

(56) References Cited

U.S. PATENT DOCUMENTS

| | | | | |
|---|---|---|---|---|
| 2,716,909 A | * | 9/1955 | Rupert | 76/107.1 |
| 3,913,420 A | * | 10/1975 | Coon | 76/13 |
| 4,227,396 A | * | 10/1980 | Crowe | 72/469 |
| 6,651,479 B1 | * | 11/2003 | Ratte | 72/476 |

* cited by examiner

Primary Examiner—Daniel C. Crane
(74) Attorney, Agent, or Firm—Alix, Yale & Ristas, LLP

(57) ABSTRACT

A metal-forming die according to the present invention includes die blades with convoluted opposed side surfaces that correspond to variable-width features on the working surface of the die. The convoluted side surfaces and variable-width working surface features permit the impression left by one die blade to fill space taken from an impression made by a laterally adjacent die blade. Such a die permits formation of working surface shapes not possible with flat-sided die components. The die is manufactured in discrete longitudinally extending components, or blades. Dividing the working surface of the die into longitudinally extending portions, each carried by a die blade allows conventional machining processes to be employed in forming the working surface on each die blade. An additional machining process cuts complementary shapes on the sides of the die blades. The die blades and their corresponding working surfaces interfit, or nest together.

6 Claims, 6 Drawing Sheets

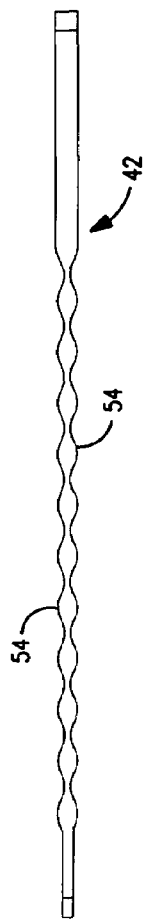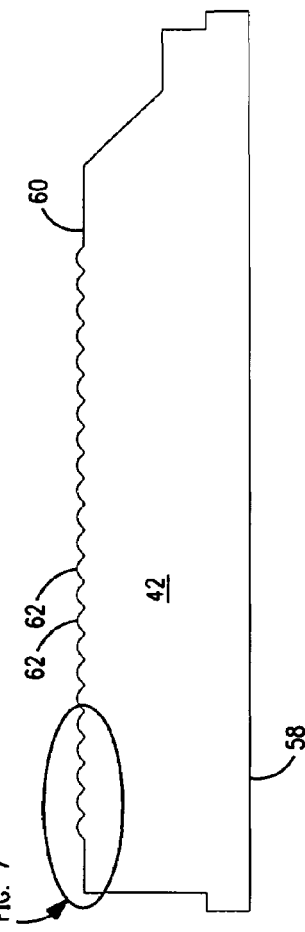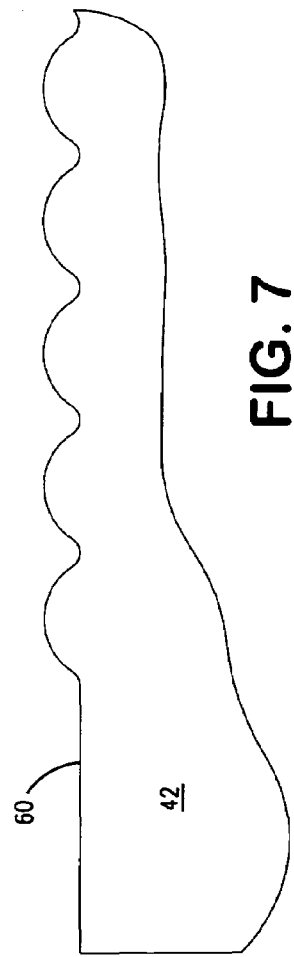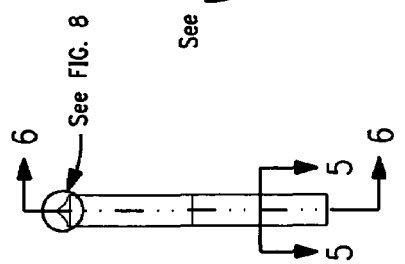
FIG. 5
FIG. 6
FIG. 7
FIG. 4

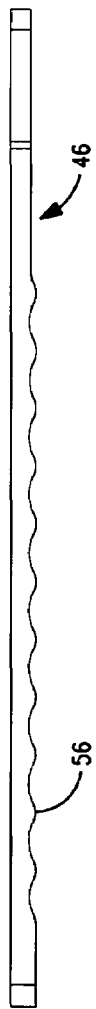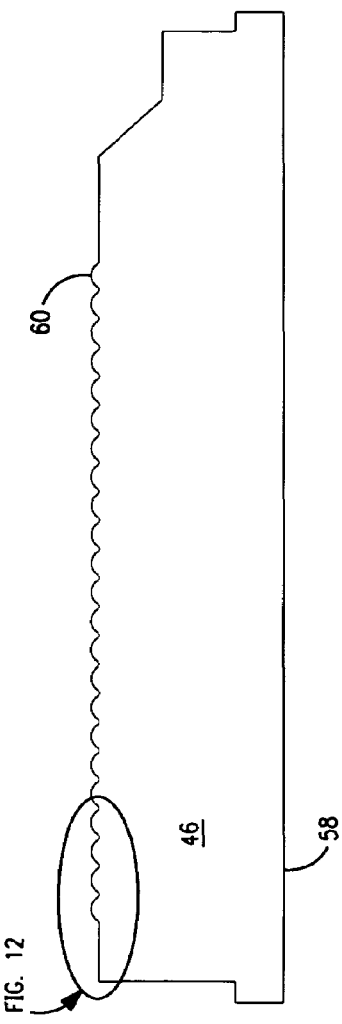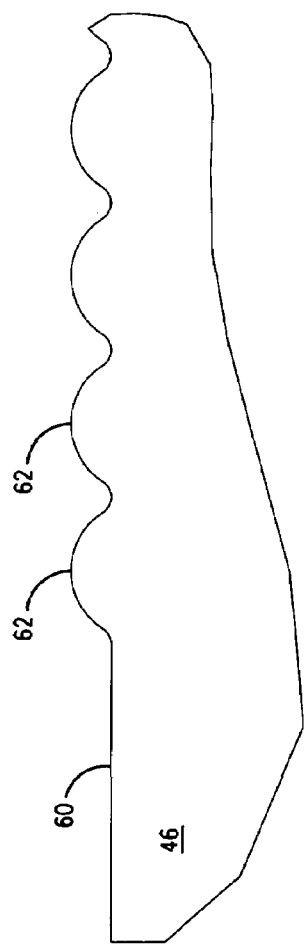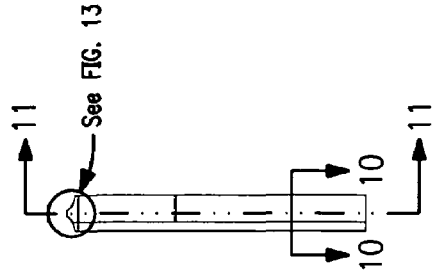

METAL-FORMING DIE AND METHOD FOR MANUFACTURING SAME

CROSS REFERENCE TO RELATED APPLICATIONS

This application is a continuation-in-part of U.S. application Ser. No. 10/782,151, filed Feb. 18, 2004, now U.S. Pat. No. 6,953,138.

BACKGROUND OF THE INVENTION

The present invention relates to cold-forming metal workpieces, and more particularly to multi-component dies for use in stamping or coining operations.

DESCRIPTION OF THE RELATED ART

The use of a press to stamp or coin metal is well known. In a typical stamping operation, a blank is placed between opposed dies and the dies are forced together by a press. The blank and the dies are configured so that when the dies are separated, the blank has taken on a desired shape. The shape of the stamped part may be three-dimensional where the imposed dies impart curvature to what is typically a flat blank.

Coining differs from a typical stamping operation in that the blank is closely confined by the dies. Confining the blank results in higher pressures that are useful in producing fine detail. The present invention relates most closely to coining operations in which a flat metal blank is impressed with a finely detailed pattern of depressions or pockets. The die or dies for a coining operation are typically finely detailed and three-dimensional. Production of such dies has been time consuming and expensive. Where the pattern to be imparted by the coining operation repeats, it is known to produce the coining die in the form of discrete parts which are clamped together to form the die for one surface of the workpiece.

An example of a product produced by a multi-component coining die is the surgical stapler anvil shown in FIG. 1. The anvil 200 defines three parallel rows of staple-forming pockets 210 along either side of a central slot. The staple-forming pockets are staggered so that the leg-clinching portion (longitudinally in the center) of a pocket in one row is laterally aligned with the leg-receiving portion (at the distal ends of each pocket 210). The anvil 200 is configured for use in a surgical stapler in which staples are driven from a staple-holding assembly opposed to the anvil, through tissue and into the pockets 210 defined by the anvil. One staple leg enters each leg-forming cup of the pocket 210 and is clinched inwardly and upwardly to secure the tissue. The position, configuration and surface quality of the staple-forming pockets 210 are important to consistent and accurate forming of the surgical staples. The surgical staple anvil of FIG. 1 is coined only on one surface.

The anvil 200 includes a repeating pattern of staple-forming pockets 210 in longitudinally extending rows. Dividing the desired anvil pocket pattern into individual linear rows allows the die blades to be produced efficiently using conventional machining operations. The coining die used to produce the anvil of FIG. 1 is assembled from a plurality of longitudinally extending die components referred to as "blades". Each blade is configured to produce one row of staple-forming pockets. The die blades are interspersed with spacers to position the pocket-forming blades in the clamp. The width of the staple-forming pockets of FIG. 1 does not vary, which allows the die blades to be formed with plana-opposed longitudinal sides. Each blade is cut, ground and polished prior to assembly into the clamp. The clamped coining die is then installed in a press. An anvil blank is rigidly supported in the press and the die is forced into the blank where it leaves an impression corresponding to the rows of pockets illustrated in FIG. 1.

While the anvil of FIG. 1 has proven effective for its intended purpose, improvements in staple-forming pocket configuration are possible. Changes in staple-forming pocket configuration have been constrained by limitations in die design and manufacture.

SUMMARY OF THE INVENTION

Briefly stated, a metal forming die according to the present invention includes die blades with convoluted opposed side surfaces that correspond to variable-width features on the working surface of the die. The convoluted side surfaces and variable-width working surface features permit the impression left by one die blade to fill space taken from an impression made by a laterally adjacent die blade. Such a die permits formation of working surface shapes not possible with flat-sided die components.

The die is manufactured in discrete, longitudinally extending components, or blades. Dividing the working surface of the die into longitudinally extending portions, each carried by a die blade, allows conventional machining processes to be employed in forming the working surface on each die blade. An additional machining process cuts complementary shapes on the sides of the die blades. The die blades and their corresponding working surfaces interfit, or nest together.

An object of the present invention is to provide a new and improved metal-forming die assembly that allows greater flexibility in the design of coined surfaces.

Another object of the present invention is to provide a new and improved method of manufacturing a metal-forming die that affords significantly improved flexibility in the design of coined surfaces with little increase in the cost of die manufacture.

A further object of the present invention is to provide a new and improved method of manufacturing a metal-forming die for the production of complex coined surfaces.

BRIEF DESCRIPTION OF THE DRAWINGS

FIG. 4 is an end plan view of a die blade according to aspects of the present invention;

FIG. 5 is a sectional view of the die blade of FIG. 4, taken along line 5—5 thereof;

FIG. 6 is a sectional view of the die blade of FIG. 4, taken along line 6—6 thereof;

FIG. 7 is an enlarged detail of FIG. 6;

FIG. 9 is an end plan view of a second die blade according to aspects of the present invention;

FIG. 10 is a sectional view of the die blade of FIG. 9, taken along line 10—10 thereof;

FIG. 11 is a sectional view of the die blade of FIG. 9, taken along line 11—11 thereof;

FIG. 12 is an enlarged detail of FIG. 11; and

DETAILED DESCRIPTION OF THE PREFERRED EMBODIMENT

Figure 1:
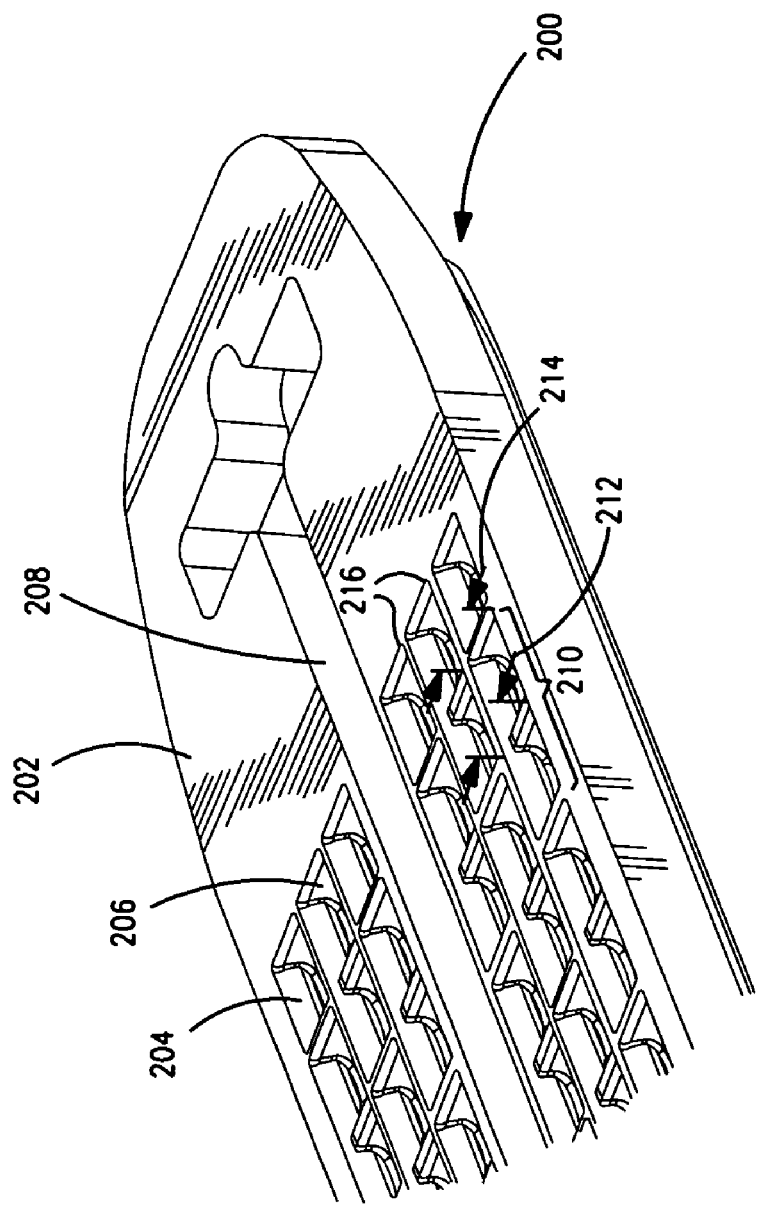
FIG. 1 is an enlarged partial perspective view of a surgical stapler anvil produced by a prior art metal-forming die.

FIG. 1 illustrates a surgical stapler anvil 200 produced by a prior art metal-forming die. The anvil 200 includes three staggered parallel rows of staple-forming pockets 210 in the top surface 202. Channeling surfaces 204 are provided to enlarge the target area for the staple legs. The lateral width 212 of the staple-clinching portion (longitudinally in the center) of each pocket 210 is the same as the lateral width 214 of the leg-receiving portion (at the distal ends of the pocket 210). The anvil 200 of FIG. 1 is configured for use in a surgical stapler which applies three staggered parallel rows of surgical staples while simultaneously cutting the tissue with a blade moving in slot 208 as is known in the art. The structure and function of such surgical staplers is well-known and will not be further discussed herein.

The anvil 200 defines three staggered rows of staple-forming pockets along either side of a blade slot 208. Each of the staple-forming pockets is principally defined by arcuate clinching surfaces 206 and substantially planar angled guide surfaces 204. The arcuate clinching surfaces 206 are substantially flat in cross section while the guide surfaces 204 are substantially planar. The pockets 210 are arranged in longitudinally extending rows such that the guide surfaces 204 of the pockets in one row meet the guide surfaces of pockets in an adjacent row to form a linear ridge 216 separating the rows of pockets from each other.

Longitudinally extending metal-forming blades are clamped with spacers to form the die that produces the pattern of pockets shown in FIG. 1. Separating the die into a plurality of longitudinally extending blades permits the efficient formation of the die working surface by conventional machining operations such as wire electrical discharge machining (EDM), grinding and polishing. When clamped together and rigidly supported in a press, the blades and spacers together define the working surface of the die which, when forced into a metal blank, leaves an impression as shown in FIG. 1.

Figure 2:
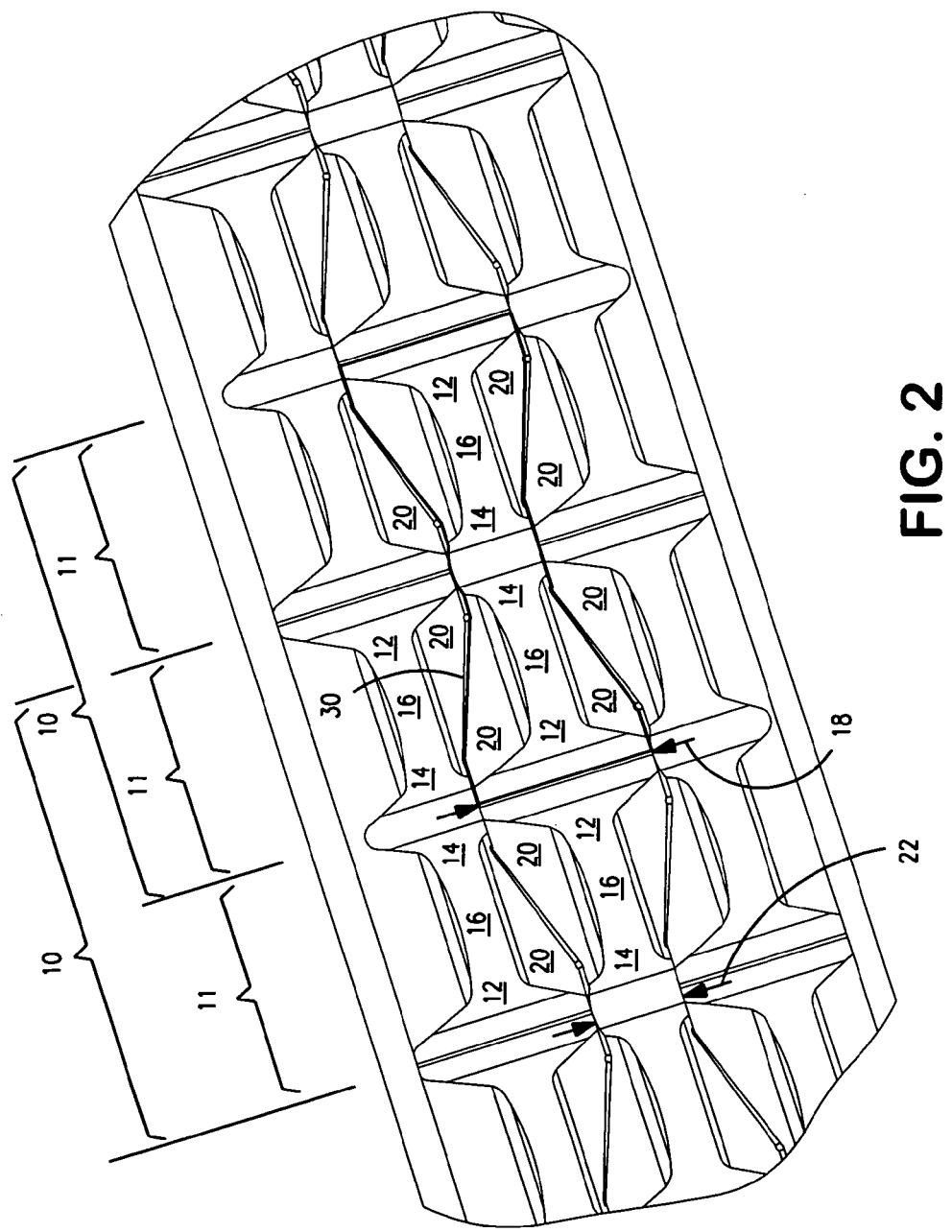
FIG. 2 is an enlarged partial perspective view of a surgical staple anvil produced by a metal-forming die according to aspects of the present invention.

FIG. 2 is an enlarged, partial view of a surgical stapler anvil formed by a die according to aspects of the present invention. FIG. 2 illustrates a portion of one side of the anvil showing three staggered parallel rows of staple-forming pockets 10. Each pocket 10 includes two mirror-image, leg-forming cups 11. Each leg-forming cup 11 is defined by a concave, arcuate clinching surface 16 extending from a descending leg-receiving portion 12 to an ascending leg-clinching portion 14. The clinching surfaces 16 are portions of an undulating surface that extends the length of each row of pockets. Guide surfaces 20 extend upwardly and outwardly from either side of the clinching surface 16 to define an expanded target area for the staple legs (not shown). The guide surfaces 20 are almost vertical where they join the clinching surface 16 in the deepest part of each leg-forming cup 11. The guide surfaces 20 flatten out to a shallow, angular orientation as they progress laterally outwardly away from the clinching surface 16.

Unlike the staple-forming pockets 210 of FIG. 1, the lateral width of each pocket 10 shown in FIG. 2 varies along its length. The lateral width 18 of the leg-receiving portions 12 at the distal ends of each pocket are laterally expanded into space that would otherwise be occupied by the leg-clinching portions 14 of a laterally adjacent pocket. In a surgical stapler, the leg-clinching portions 14 do not benefit from added lateral width since the staple leg has already been partially formed and is aligned with the clinching surface 16 when it comes into contact with the ascending leg-clinching portion 14 of the pocket. The pocket formation shown in FIG. 2 can be described as "nested" because the laterally expanded leg-receiving portion 12 of one pocket fits into a reduced lateral width 22 of the leg-clinching portion 14 of an adjacent pocket. The guide surfaces 20 of adjacent rows of staple-forming pockets meet along a convoluted intersection 30.

Aspects of the present invention relate to particular die blade configurations that produce the nested staple-forming pockets shown in FIG. 2.

Figure 3:
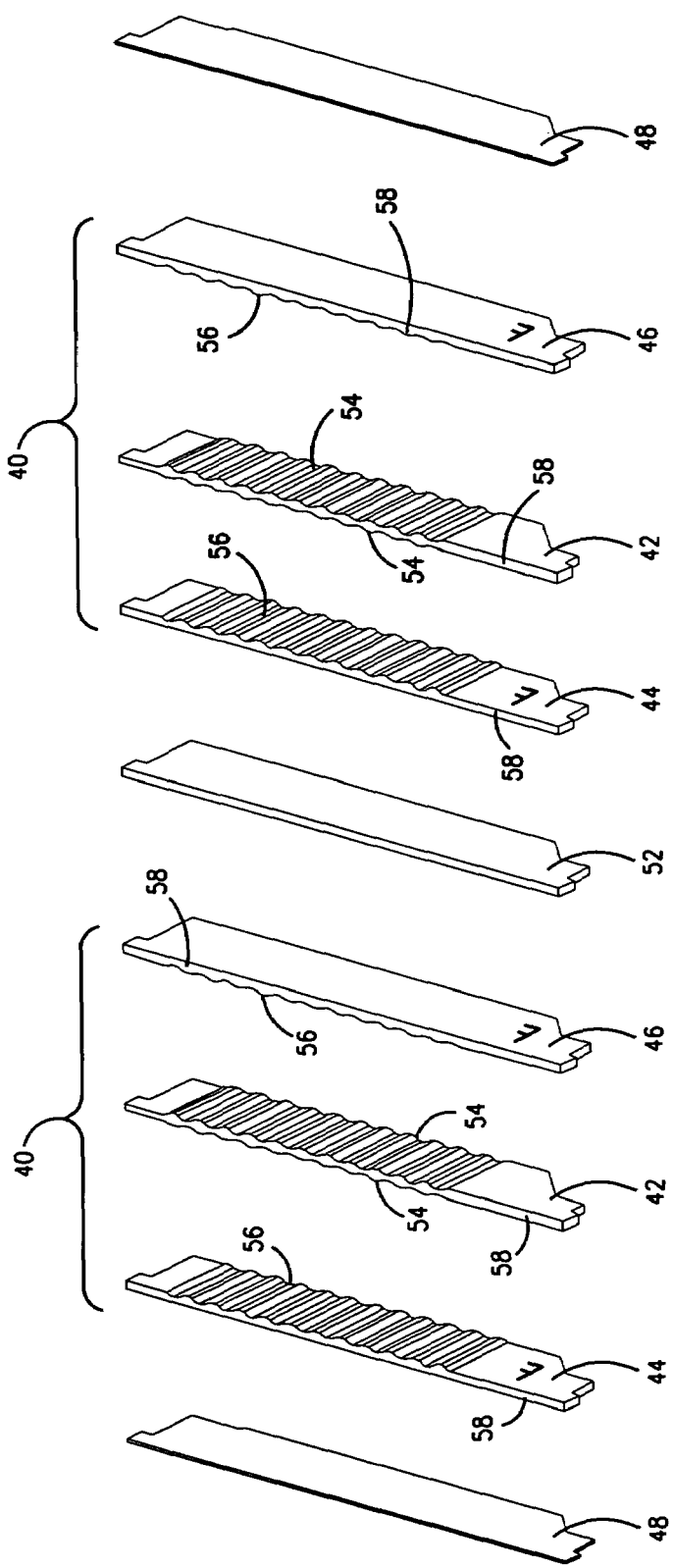
FIG. 3 is an exploded perspective view of a metal-forming die according to aspects of the present invention.
Figure 13:
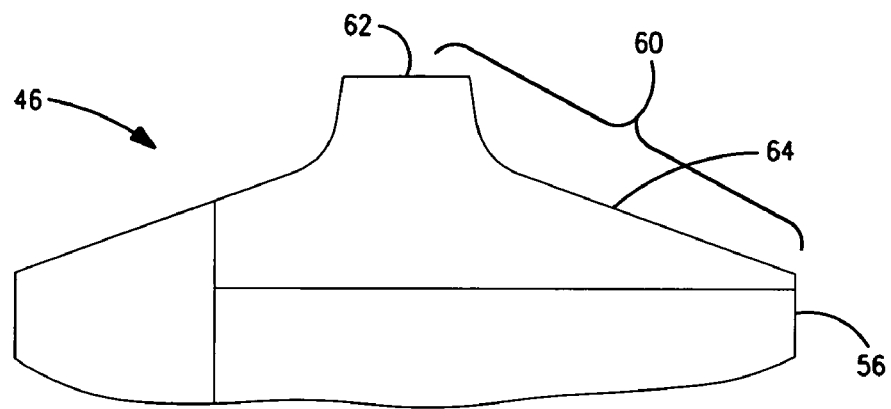
FIG. 13 is an enlarged detail of FIG. 9.
Figure 8:
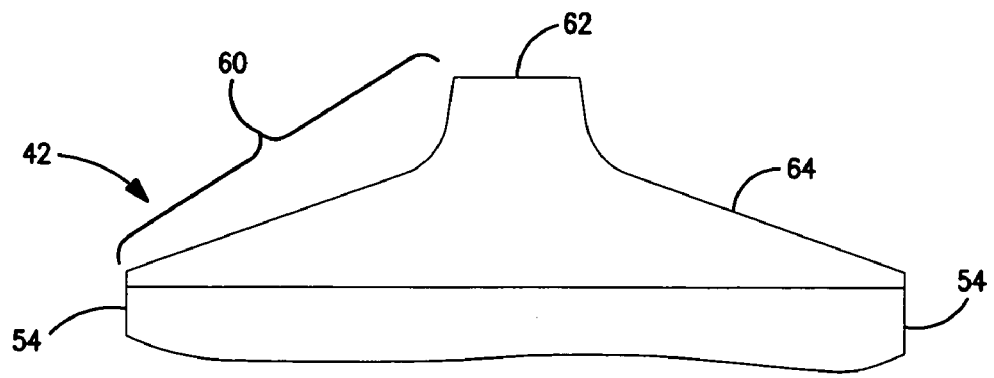
FIG. 8 is an enlarged detail of FIG. 4.

FIG. 3 illustrates blades 42, 44, 46 and spacers 48, 52 which are clamped together to form a die which leaves an impression as shown in FIG. 2. An aspect of the present invention relates to shaping the sides of each pocket-forming blade to correspond to the convoluted interface 30 between the rows of pockets. Relatively thin spacers 48 are used to center the pocket-forming blades in a clamping device called a chase (not shown). The center spacer 52 separates one set 40 of three pocket-forming blades 42, 44, 46 from the other and corresponds to a lateral spacing slightly greater than the slot in the center of the anvil. The convoluted sides 54, 56 of the pocket-forming blades 42, 44, 46 fit together like puzzle pieces.

Manufacturing die blades with convoluted sides requires an additional machining step. In a preferred method, wire EDM is used to cut at least one side of each pocket-forming blade 42, 44, 46 into the convoluted shape shown in FIGS. 3, 5 and 10. The center pocket-forming blade 42 has the convoluted shape on both sides 54, while the laterally inner and outer blades 44, 46 of each three blade set 40 are convoluted only where they interface with the sides 54 of the center blade (sides 56).

FIGS. 4–8 illustrate one of the center pocket-forming blades 42. The working surface 60 of the pocket-forming blade 42 is a positive version of one row of the concave staple-forming pockets 10. The blade begins as a planar blank. The bumps 62 shown in FIGS. 6 and 7 correspond to the clinching surface 16 of FIG. 2. The bumps 62 are cut by wire EDM onto the blank. The convoluted side surfaces 54 of the blade as shown in FIG. 5 are then produced by wire EDM. The bump surfaces 62 are polished. Material is removed along either side of the blade to form the die surfaces 64 that correspond to the guide surfaces 20 of the staple forming pockets 10. In the preferred method, this material is removed by grinding. In a final step, the die surfaces 64 are polished. A polished working surface of the die produces smooth pocket surfaces on the formed part.

FIGS. 9–13 illustrate the configuration of one of the outside blades 46. There are two such outside blades 44, 46 in each three-blade set 40. The two outside blades 44, 46 are mirror images of each other.

The multi-part structure of the die can produce more complex impressions than was possible with flat-sided blades. The improved die blades according to the present invention are still manufactured using standard machining processes. The additional machining step required to produce die blades with convoluted, interfitting side surfaces is a conventional one and still far less expensive than producing the die in a single unit by some other manufacturing method. As an additional benefit, the interfitting sides 54, 56 of the blades 42, 44, 46 maintain longitudinal alignment of adjacent rows of pockets more accurately than flat-sided blades.

While a preferred embodiment of the foregoing invention has been set forth for purposes of illustration, the foregoing description should not be deemed a limitation of the invention herein. Accordingly, various modifications, adaptations and alternatives may occur to one skilled in the art without departing from the spirit and the scope of the present invention.

The invention claimed is:

1. A metal-forming die comprising:
 a plurality of blades extending in a first direction, each said blade having a working surface, opposed side surfaces extending away from said working surface and forming contacting surfaces between adjacent blades, a width measured between said opposed side surfaces and a rear surface opposed to said working surface, the working surface of at least one of said blades defining features to be formed on a workpiece, at least one of said features being a first variable-width feature having a lateral dimension which varies along the length of said blade,
 wherein the width of said at least one blade varies with the lateral dimension of said first variable-width feature and the side surfaces of adjacent blades are complementary to the variable width of said at least one blade.

2. The metal-forming die of claim 1, wherein said first variable-width feature comprises an expanded lateral dimension and the working surface of a blade adjacent said at least one blade includes a second variable-width feature to be formed on the work piece,
 wherein said second variable-width feature comprises a reduced lateral dimension and said expanded lateral dimension of said first variable-width feature is laterally adjacent to said reduced lateral dimension of said second variable-width feature.

3. The metal-forming die of claim 1, wherein the width of said at least one blade is substantially constant from said working surface to said rear surface.

4. A method of manufacturing a metal-forming die adapted for use in a press, said die comprising a plurality of adjacent die bodies having longitudinally extending working surfaces, opposed side surfaces extending from said working surface and a width between said opposed side surfaces, said die bodies clamped together with said side surfaces against one another and adjacent working surfaces defining a forming surface of the die, said method comprising:
 forming a variable-width feature on the working surface of at least one die body, said variable-width feature having a lateral dimension which varies along the length of said at least one die body;
 shaping the opposed side surfaces of said at least one die body so that the width between said side surfaces is substantially equal to a corresponding lateral dimension of said variable-width feature;
 forming a second variable-width feature on the working surface of a die body, said second variable-width feature having a lateral dimension which varies along the length of said die body;
 shaping the opposed side surfaces of said die body so that the width between said side surfaces is substantially equal to a corresponding lateral dimension of said second variable-width feature.

5. The method of claim 4, comprising:
 configuring the side surface of a die body adjacent one of the opposed side surfaces of said at least one die body to be complementary to said one of the opposed side surfaces.

6. The method of claim 4, comprising:
 forming a variable-width feature having an expanded lateral dimension on at least one die body; and
 forming a second variable-width feature having a reduced lateral dimension on a die body next to said at least one die body such that the expanded lateral dimension of said variable-width feature corresponds to a reduced lateral dimension of said second variable-width feature.

* * * * *